(12) United States Patent
Ledoux et al.

(10) Patent No.: US 6,660,681 B1
(45) Date of Patent: Dec. 9, 2003

(54) VANADIUM PHOSPHORUS OXIDE CATALYST HAVING A THERMALLY CONDUCTIVE SUPPORT

(75) Inventors: Marc J. Ledoux, Strasbourg (FR); Baudain Heinrich, Schiltigheim (FR); Jan Joseph Lerou, Orange, TX (US); Claude Crouzet, Strasbourg (FR); Christophe Bouchy, Folschiviller (FR); Kostantinos Kourtakis, Swedesboro, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/958,584

(22) PCT Filed: Apr. 14, 2000

(86) PCT No.: PCT/US00/09905
§ 371 (c)(1),
(2), (4) Date: Oct. 9, 2001

(87) PCT Pub. No.: WO00/62925
PCT Pub. Date: Oct. 26, 2000

Related U.S. Application Data

(60) Provisional application No. 60/129,411, filed on Apr. 15, 1999.

(51) Int. Cl.$^7$ .................. B01J 27/198; B01J 31/00; B01J 27/24; B01J 21/02
(52) U.S. Cl. ................ 502/209; 502/172; 502/200; 502/202
(58) Field of Search .............. 502/209, 200, 502/202, 172

(56) References Cited

U.S. PATENT DOCUMENTS

| | | | | |
|---|---|---|---|---|
| 4,016,105 A | * | 4/1977 | Kerr | 252/437 |
| 4,123,388 A | * | 10/1978 | Kerr et al. | 252/437 |
| 4,179,404 A | * | 12/1979 | Barone | 252/435 |
| 4,564,607 A | * | 1/1986 | Yoneda et al. | 502/209 |
| 4,677,084 A | * | 6/1987 | Bergna | 502/8 |
| 4,769,477 A | * | 9/1988 | Bergna | 549/259 |
| 4,849,539 A | * | 7/1989 | Bergna | 558/323 |
| 5,543,532 A | * | 8/1996 | Kourtakis et al. | 549/260 |
| 5,750,777 A | * | 5/1998 | Aubry et al. | 562/549 |
| 6,114,274 A | * | 9/2000 | Bordes et al. | 502/209 |

FOREIGN PATENT DOCUMENTS

| | | |
|---|---|---|
| EP | 0757024 A1 | * 2/1997 |
| EP | 0799795 A2 | * 10/1997 |
| EP | 0803470 A1 | * 10/1997 |

* cited by examiner

Primary Examiner—C. Melissa Koslow
Assistant Examiner—Patricia L. Hailey

(57) ABSTRACT

A catalyst comprising vanadium phosphorus oxide combined with a thermally conductive material is particularly useful for the selective hydrocarbon oxidations (e.g., butane to maleic anhydride) and can be prepared by forming a suspension comprising a vanadium (IV) phosphate compound in a liquid medium (via hydrochloric acid digestion of $V_2O_5$ and $H_3PO_4$ in an aqueous solvent or via heating vanadium pentoxide with at least one substantially anhydrous unsubstituted alcohol having 1–10 carbon atoms, 1–3 hydroxyl groups free from olefinic double bonds to form a feed of vanadium pentoxide reduced to a valence between 4 and 4.6, and then contacting the feed with a solution of orthophosphoric acid and at least one unsubstituted alcohol), adding a thermally conductive material to the suspension under agitation at moderated temperature between 40° C. and 120° C., followed by drying, optionally but preferably washing and calcining (either in situ or ex situ) the material thus formed.

7 Claims, 2 Drawing Sheets

VANADIUM PHOSPHORUS OXIDE CATALYST HAVING A THERMALLY CONDUCTIVE SUPPORT

This application claims the benefit of Provisional application No. 60/129,411 field Apr. 15, 1999

1. Field of the Invention

This invention relates to supported vanadium phosphorus oxide catalysts and a process for their preparation.

2. Technical Background

Maleic anhydride is used as a raw material for numerous products, including agricultural chemicals, paints, paper sizing, food additives and synthetic resins. To fill the high demand for this valuable chemical, a variety of commercial processes have been developed for its production, the most successful of which involves the vapor phase oxidation of n-butane to maleic anhydride in the presence of a vanadium phosphorus oxide ("VPO") catalyst. Since the development of this method in the 1970's, research has continued to improve the reaction conditions and, particularly, the VPO catalysts.

A review of the improvements made in this technology is given by G. J. Hutchings, *Applied Catalysis*, 72(1991), Elsevier Science Publishers B. V. Amsterdam, pages 1–31. The preferred method of preparation of VPO catalysts is the hydrochloric acid digestion of $V_2O_5$ and $H_3PO_4$ in either an aqueous solvent, as described, for example, in U.S. Pat. No. 3,985,775, or non aqueous solvent, such as methanol, tetrahydrofuran (THF) or isobutanol, followed by solvent removal to give what is termed the catalyst precursor, vanadium hydrogen phosphate, $VO(HOPO_4).(H_2O)_{0.5}$. The precursor is then activated by heating, as described, for example, in U.S. Pat. No. 3,864,280 and U.S. Pat. No. 4,043,943. Further optimization of the preparation is described in U.S. Pat. No. 4,132,670, whereby vanadium pentoxide is heated with a selected anhydrous unsubstituted alcohol, adding an orthophosphoric acid to form the catalyst precursor and calcining the precursor to obtain the catalyst having high intrinsic surface area. Further attempts to improve the VPO catalyst performance by the use of dopants and/or supports are described in U.S. Pat. No. 4,442,226 and U.S. Pat. No. 4,778,890.

Vanadium, phosphorus and oxygen can form a large number of distinct compounds which have been well characterized, e.g., $\alpha$-$VOPO_4$, $\gamma$-$VOPO_4$, $VOHPO_4$, $(VO)_2P_2O_7$, $VO(PO_3)_2$ and $VO(H_2PO_4)_2$. The most active catalytic phase is believed to be $(VO)_2P_2O_7$, which is also the predominant oxide phase in VPO catalysts. Nevertheless, VPO catalysts are usually referred to as "mixed oxides" in recognition of the probable presence of other oxide phases. VPO catalysts typically have V:P atomic ratios in the range of 1:1 to 1:2 and have an average bulk vanadium oxidation state in the range of 4.0–4.3.

Guliants et al., *Catalysis Today*, 28 (1996), pages 275–295, studied the effect of the phase composition of VPO catalysts on their effectiveness as catalysts for the oxidation of n-butane to maleic anhydride. This work indicated that the best performihng VPO catalyst was prepared from vanadyl hydrogen phosphate hemihydrate precursor that was free of microcrystalline or amorphous phases, such as $VO(H_2PO_4)_2$ and $\delta$-and $\gamma$-vanadyl (V) orthophosphates. It was disclosed that these undesirable components could be removed by washing either the precursor or the catalyst with boiling water.

While numerous modifications have been made to improve performance of VPO catalysts, VPO has a low thermal conductivity. With the high temperatures of reaction used in the vapor phase oxidation of n-butane to maleic anhydride and the large amounts of heat released, the catalysts deteriorate in activity over time.

SUMMARY OF THE INVENTION

In one aspect, the invention provides a catalyst comprising vanadium phosphorus oxide combined with a thermally conductive material. Vanadium phosphorus oxide compounds can be exemplified by vanadyl pyrophosphate, however, it should be noted that any vanadium phosphorus oxide compounds which are catalytically active can be used in the catalyst. The thermally conductive material has a thermal conductivity of at least 1 W meter$^{-1}$ K$^{-1}$. Typically the conductive material is selected from the group consisting of silicon nitride, boron nitride, phosphorus treated boron nitride, aluminum nitride and mixtures thereof.

In another aspect, the invention comprises a process for preparing a catalyst comprising vanadium phosphorus oxide combined with a thermally conductive material, the process comprising the steps of:

a) forming a suspension comprising a vanadium (IV) phosphate compound in a liquid medium;

b) adding a thermally conductive material to the suspension under agitation at a temperature between 40° C. and 120° C. to provide vanadium phosphorus oxide precursor combined with the thermally conductive material;

c) drying the vanadium hydrogen phosphate precursor /thermally conductive material;

d) optionally but preferably washing the dried vanadium phosphorus oxide precursor/thermally conductive material with water;

e) calcining the vanadium phosphorus oxide precursor at elevated temperature (150° C., for 12–15 hours) to obtain a catalyst comprising vanadium phosphorus oxide combined with a thermally conductive material;

f) calcination at 380° C., hours, air;

g) activation in butane/air (1.5% butane/air =13.1% O2/butane), for 15 hours;

h) additional activation at 420° C., 1020 h-1 (1.5% butane/air) for 100 hours; and i) stabilization for an additional 50 hours under reaction conditions.

It is an object of this invention is to further advance the technology of VPO catalysis by providing for a VPO catalyst combined with a thermally conductive material particularly effective for hydrocarbon oxidation.

DETAILED DESCRIPTION OF THE INVENTION

Catalyst

Figure 1:
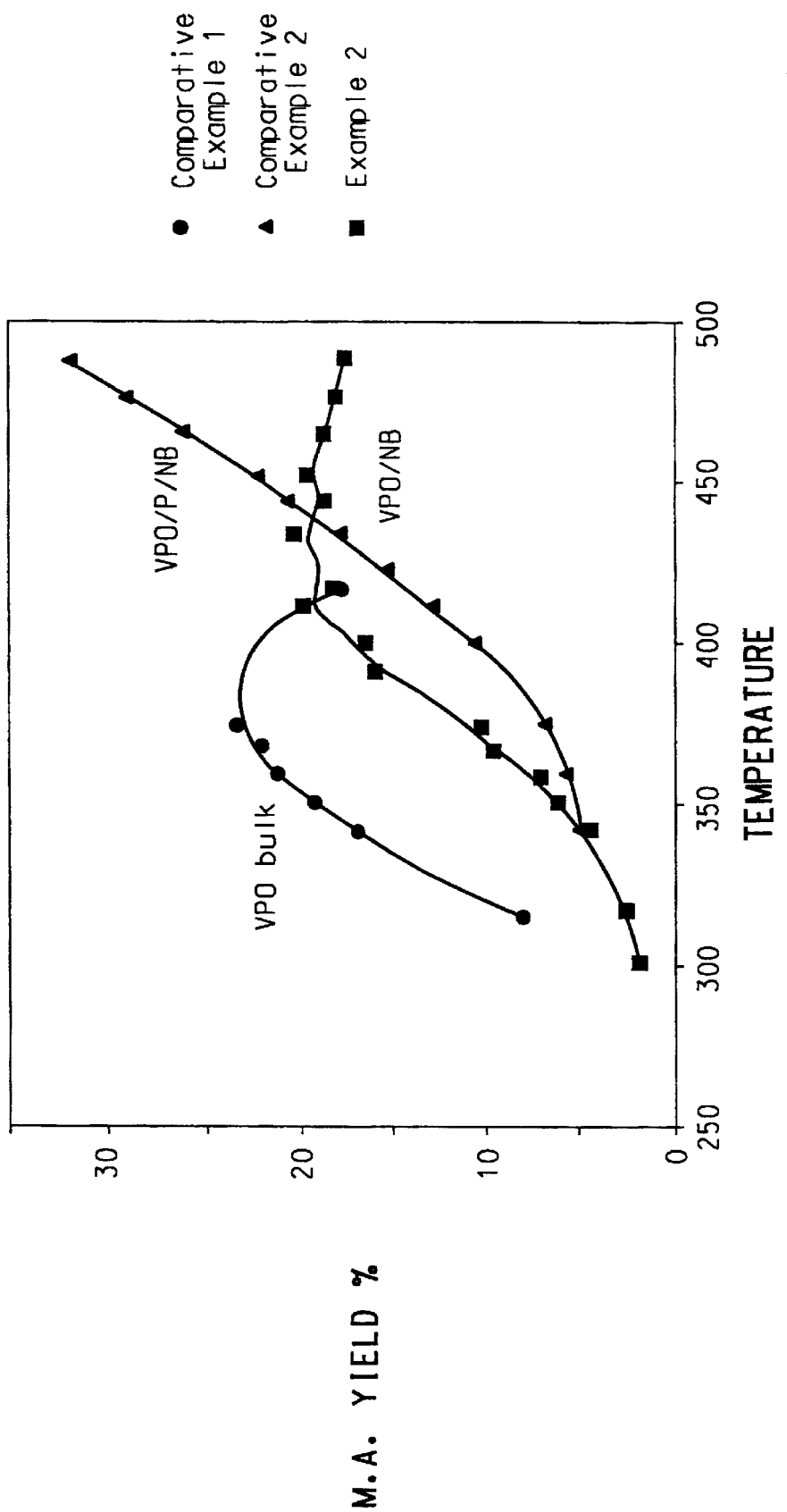
FIG. 1 is a plot of the yield of maleic anhydride versus reaction temperature for the oxidation of n-butane using vanadium phosphorus oxide catalysts combined with boron nitride compared to phosphorus treated boron nitride and vanadium phosphorus oxide. Data from Comparative Example 2 (vanadium phosphorus oxide) and Examples 1 (vanadium phosphorus oxide supported on boron nitride are shown in this figure.

The catalyst of this invention comprises vanadium phosphorus oxide combined with a thermally conductive material. By "vanadium phosphorus oxide", it is meant a compound containing the elements vanadium, phosphorus and oxygen, and which is catalytically active in exothermic catalytic reactions, especially hydrocarbon oxidations. Vanadium pyrophosphate is an example of such compounds that may be useful. The vanadium phosphorus oxide may contain promoters, especially those known to improve activity in hydrocarbon oxidations, such as those described in G. J. Hutchings, *Applied Catalysis*, 72 (1991), Elsevier Science Publishers B. V. Amsterdam, pages 1–31. Further the compounds can comprise silica as a result of treatment by methods known to enhance attrition resistance, such as described in Bergna, U.S. Pat. No. 4,677,084.

The vanadium phosphorus oxide compound of this invention is combined with a thermally conductive material. By a "thermally conductive material", it is meant a material having a thermal conductivity of at least 1 W meters$^{-1}$K$^{-1}$, preferably at least (or between to provide a range) 10 W meter$^{-1}$ K$^{-1}$. The thermally conductive material is typically selected from the group consisting of, silicon nitride, boron nitride, phosphorus-modified boron nitride, aluminum nitride, and the like.

The amount of vanadium phosphorus oxide in the catalyst should be in the range of 0.1 to 90 wt %, based on the total weight of the catalyst. Preferably the vanadium phosphorus oxide is present in an amount of 5 to 50 wt %, and most preferably 10 to 40 wt %.

Commercially available thermally conductive materials can be used. These include silicon nitride, and boron nitride. As described in this invention, preferably boron nitride is boron nitride treated with a phosphorous containing compound. The catalysts can be in any form wherein vanadium phosphorus oxide is combined with, for example, or intimately associated with, the thermally conductive support. Preferably, the catalyst will comprise a "core" of the thermally conductive material, a "shell" of the vanadium phosphorus oxide compound and a transition phase intermediate between the core and the shell which contains the elements of the thermally conductive material, and vanadium, phosphorus and oxygen. However, the catalysts may also be in a form wherein the vanadium phosphorus oxide is bound to the thermally conductive material, in such a manner where no transition phase can be seen.

A chemical reaction of the vanadium phosphorus oxide catalyst onto the thermally conductive material is preferred. Mechanical mixing of the vanadium phosphorus oxide with the thermally conductive material is also possible.

Process to Prepare Catalyst

In the process of this invention, first a suspension of vanadium (IV) phosphate in a liquid medium is formed. Preferably the liquid medium comprises with at least one substantially anhydrous unsubstituted alcohol having 1–10 carbon atoms, 1–3 hydroxyl groups and free from olefinic double bonds. Vanadium phosphorus oxide precursor is prepared by mixing vanadium pentoxide with the alcohol-containing medium, and heating the mixture to form a feed of vanadium oxide reduced to a valence of between 4 and 4.6. The vanadium oxide feed is then contacted with a solution comprising orthophosphoric acid and at least one substantially anhydrous unsubstituted alcohol having 1–10 carbon atoms, 1–3 hydroxyl groups and free from olefinic double bonds. Mixing of the vanadium oxide with the orthophosphoric acid solution forms a suspension of vanadium phosphorus oxide precursor, as taught in U.S. Pat. No. 4,132,670, the disclosure of which is incorporated herein by reference. Alternatively, the liquid medium comprises water and vanadium (IV) phosphate can be formed by the hydrochloric acid digestion of $V_2O_5$ and $H_3PO_4$ in an aqueous solvent, as described, for example, in U.S. Pat. No. 3,985,775, the disclosure of which is incorporated herein by reference. Any commercially available vanadium pentoxide, orthophosphoric acid and anhydrous alcohol of the type described above can be used in the practice of this process.

A thermally conductive material is added to a suspension containing the vanadium phosphorus oxide precursor (formed by refluxing the mixture of $V_2O_5$ and orthophosphoric acid for 1–4 hours) under agitation. The thermally conductive material is maintained between a temperature between 40° C. and 120° C. to form vanadium (IV) phosphate combined with the thermally conductive material. During this step, the rapid crystallization of the vanadium (IV) phosphate should be avoided, as that would result in a mixture of crystallized vanadium (IV) phosphate and the thermally conductive material, rather than the of this invention.

As the reaction continues, some of the solvent may evaporate and the reaction mixture may begin to thicken. Typically, the reaction mixture is placed under partial vacuum at a temperature above 125° C. to dry the mixture to the consistency of a non-dry mud and may still be washed with relative ease.

The resulting material is optionally but preferably washed with water to extract the $VO(H_2PO_4)_2$ phase from the precursor. The presence/absence of the $VO(H_2PO_4)_2$ phase is monitored by the use of X-ray diffraction in accordance with Guliants et al., *Catalysis Today*, 28 (1996), pages 275–295, incorporated herein by reference. After washing, the material consists essentially of catalyst precursor, vanadium hydrogen phosphate, $VO(HOPO_3).(H_2O)_{0.5}$ combined with the thermally conductive material.

The catalyst is then formed from the precursor by heating the precursor in air, followed by heating in a mixture of air and hydrocarbon in accordance with the procedure described in the aforementioned. U.S. Pat. No. 4,132,670. To insure that the catalyst is fully stabilized for use in the oxidation of hydrocarbons, it is preferred that the catalyst be exposed to a mixture of air and hydrocarbon for a period of at least 50 hours and preferably at least 100 hours. This may be done in situ or ex situ.

The catalysts of this invention may be further processed to impart attrition resistance by methods known in the art, such as, for example, by applying a coating of $SiO_2$ in accordance with U.S. Pat. No. 4,677,084, the disclosure of which is incorporated herein by reference. This further process is particularly applied when the thermally conductive material is in the form of a fine powder.

The catalysts of this invention are well suited for use as catalysts in exothermic reactions, especially hydrocarbon oxidations, in any type of reactor, for example, fixed bed, fluidized bed and recirculating solids reactor. In particular because the thermally conductive support acts as a heat sink, the catalysts of this invention can be utilized at higher temperatures than the corresponding catalyst in the absence of thermally conductive material. More specifically, the catalyst is well suited to be efficiently utilized in fixed bed reactors with improved selectivity at high butane concentrations.

EXAMPLES

COMPARATIVE EXAMPLE 1

A suspension containing 5.0013 g of $V_2O_5$ (99.5%, available from Strem, 93–231, Newbury Port, Mass.), 20 ml of isobutanol (99.5%, available from Fluka, 58448, Fuchs, Switzerland) and 13 ml of benzyl alcohol (available from Fluka, 13170, Buchs, Switzerland) was heated under reflux at 120–130° C. for three hours to generate $V_2O_4$ in accordance with the following reactions:

isobutanol+$V_2O_5$→isobutanol+$V_2O_4$+$H_2O$ benzyl alcohol+$V_2O_5$→benzaldehyde+$V_2O_4$+$H_2O$ The water generated from the reactions was removed by a conventional Dean-Stark trap. The resulting solution was then cooled to 20° C. and a solution of 7.448 g of $H_3PO_4$ (98%, available from Aldrich, 31,027-2, Milwaukee, Wis.) in 10 ml of isobutanol was added dropwise to the solution with stirring. The solution was then heated to 120–130° C. under reflux until a strong blue-green color appeared in accordance with the reaction below.

2$H_3PO_4$+$V_2O_5$→2(VO)$HPO_4$.0.5 $H_2O$+$H_2O$

Vanadium (IV) Phosphate Hemihydrate

Silicon carbide was provided in the form of grains having a particle size of <0.3 mm. Under vigorous agitation, 10 g of silicon carbide at 80° C. was added to he solution (10 g of silicon carbide) prepared according to U.S. Pat. No. 5,460,759 and 5,427,761 was added as a hot powder to the hot reflux containing the vanadium hydrogen phosphate hemihydrate suspension in the solvent. The temperature was increased to 130° C. for approximately 15 minutes, which led to some evaporation of the solvent. When the temperature of the mixture reaches about 135° C. the drying process was engaged under partial vacuum to obtain a suspension having a "mud"-like consistency, which was placed in a glass vessel and dried at 150° C. for 12–15 hours in air.

The dried material was crushed and sieved through a 40 microm ($4 \times 10^{-5}$ meter) sieve to eliminate particles less than 40 micron in size. At this point the sieved material was vanadium (IV) phosphate hemihydrate and VO($H_2PO_4$)$_2$ combined with silicon carbide. This sample was washed four times in hot water (90° C.) to extract the VO($H_2PO_4$)$_2$ phase which appears on the X-ray diffraction pattern of the unwashed hemihydrate. After four washes, the VO($H_2PO_4$)$_2$ phase is removed as determined by powder X-ray diffraction. The washed material was subjected to activation in accordance with the teachings of U.S. Pat. No. 4,132,670, by heating the material to a temperature of 380° C. at 3° C. per minute under air flow rate of 1.5 cc per minute and held at 380° C. for 2 hours. The material was then heated to a temperature of 480° C. at 3° C. per minute under air/butane (1.5% by volume of butane) flow rate of 3 cc per minute and held at 480° C. for 15 hours. The material was allowed to cool to 420° C. under air/butane (1.5% by volume of butane) flow of 17 cc per minute for 100 hours. This produced an "activated catalyst". The activated catalyst was further stabilized by subjecting the catalyst to 200 hours of the air/butane flow at 420° C. The activated catalyst contained 30 wt % vanadium phosphorus oxide; 30 wt % (VO)$_2P_2O_7$, 70 wt % SiC; based on V, P determined by atomic absorption (AA).

Catalytic reactions were carried out using an automated continuous flow fixed-bed microreactor system. The reactor consisted of a 6.35 mm o. d. stainless steel tube having an internal diameter of 4.57 mm. Heating the reactor tube was achieved by placing it in an isothermal fluidized sandbath in which silicon carbide was used as the fluidized heat transfer medium. The reactor temperature was controlled by monitoring the external microreactor wall temperature at the midpoint of the catalyst bed. In a typical experiment, the reactor was packed with about 0.50 g of 0.125 mm to 0.5 mm particles of supported catalyst or catalyst precursor.

Catalytic tests were run on the stabilized material and compared to a conventional bulk VPO catalyst, prepared in accordance with the process described in U.S. Pat. No. 4,132,670. Catalyst testing was based on performance of the catalysts in the oxidation of n-butane to maleic anhydride. The oxidation reactions were performed at temperatures ranging from 310 to 470° C. The feed gas contained oxygen and n-butane at a ratio of oxygen to n-butane of 1.4 to 1.5:1, contact time=1.04 seconds. The gas composition is 64% He, 18.6% 02, 12.9% butane; this is the exact feed composition for FIGS. 2, 3, 4; ratio of oxygen to butane, $O_2$/Butane=1.44. Volume of catalyst, 0.85 cc. Total flow 35 sccm; weight=0.4 g.

Blank experiments were performed using the empty reactor and the reactor filled with silicon carbide. Negligible conversion of n-butane to combustion products occurred over the temperature range of 330° C. to 450° C. when the reactor was empty. When the reactor was filled with silicon carbide, less then −3% conversion of n-butane to combustion products results.

Analyses were performed using a Hewlett-Packard Model 5890 Series II gas chromatograph equipped with both a flame ionization detector (FID) and a thermal conductivity detector (TCD). The FID was used for analysis of hydrocarbons and oxygenates. The TCD was used for analysis of gases, which included oxygen and nitrogen, carbon dioxide, carbon monoxide, water and n-butane. Methane as a standard was introduced after the reaction stream to obtain an accurate oxygen and carbon mass balance. In all cases, the mass balance is greater than 90%.

COMPARATIVE EXAMPLE 2

A five liter round bottom flask was equipped with an addition funnel, mechanical stirrer, and a reflux condensor. For the duration of the reflux, nitrogen gas was used to purge the apparatus. In an inert atmosphere drybox containing nitrogen gas, 299.6 g of air micronized vanadium pentoxide (Aldrich Chemicals, Milwaukee, Wis.) was added to the round bottom flask. To this mixture, 285 ml of benzyl alcohol (anhydrous, Aldrich Chemicals) and 3105 ml of isobutyl alcohol (anhydrous, Aldrich Chemicals) were added. The round bottom flask was then plugged with a glass stopper and brought outside of the drybox. Anhydrous phosphoric acid was prepared in the inert atmosphere drybox by mixing 257.4 g of 85+% phosphoric acid (J. T. Baker and Co., Phillipsburg, N.J.) with 99.6 g of anhydrous phosphorus pentoxide (J. T. Baker). The anhydrous phosphoric acid was then added to the addition funnel, brought outside of the drybox, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids were then filtered in a buchner funnel and dried in flowing nitrogen at 80–125° C. for a period of 16 hours to yield the catalyst precursor.

Following this procedure, the precursor was calcined and activated in a small, 4 cm fluidized bed reactor. Prior to the activation, fine particles were sieved out on a 400 mesh screen. The calcination/activation procedure was accomplished using the following conditions:

a) 25–390° C. in air b) 390° C., 1 hour in air c) 390° C. 1 hour is 1.5% butane/air
d) 390–460° C., 20 minutes in 1.5% butane/air
e) 460–460° C., 18 hours in 1.5% butane/air
f) 460–420° C. in 1.5% butane/air
g) 420–360° C. in 1.5% butane/air
h) 360–25° C. in $N_2$.

EXAMPLE 1

Solid $H_3PO_4$ grain, was dissolved in 10 ml of anhydrous isobutanol. The solution was heated to 100° C. and maintained at this temperature until all of the phosphoric acid was dissolved. The hot solution was added to 5 grams of boron nitride (BN=0.44 mm, Johnson Matthey 14102, commercial boron nitride), which had been at room temperature, with vigorous agitation. The phosphoric acid/boron nitride mixture was stirred for 30 minutes.

The resulting material was (not filtered) dried at 120° C. in air and washed three times in water to extract any excess phosphoric acid. The material was calcined at 150° C. for 12 hours in air to provide phosphorus-modified boron nitride.

Vanadium phosphorus oxide precursor in isobutanol was prepared in the same manner as in Comparative Example 1. The phosphorus-modified boron nitride was added to the vanadium (IV) phosphate mixture under agitation at a temperature between 100° C. and 150° C. to form vanadium phosphorus precursor supported on the phosphorus-modified boron nitride (VPO/PIBN). During the mixing process some of the isobutanol solvent evaporated and the mixture thickened. The reaction mixture was placed under partial vacuum (20 torr) at a temperature above 120° C. to dry the mixture to a consistency of non-dry mud. The mixture was then dried, crushed, sieved, and washed as described above in Comparative Example 1 to provide phosphorus-modified boron nitride supported vanadium phosphorus oxide precursor.

The supported vanadium phosphorus oxide precursor was subjected to activation in accordance with the teachings of U.S. Pat. No. 4,132,670, by heating the material to a temperature of 380° C. at 3° C. per minute under air flow rate of 1.5 cc per minute and held at 380° C. for 2 hours. The material was then heated to a temperature of 480° C. at 3° C. per minute under air/butane (1.5% by volume of butane) flow rate of 3 cc per minute and held at 480° C. for 15 hours. The material was allowed to cool to 420° C. under air/butane (1.5% by volume of butane) flow of 17 cc per minute for 100 hours. This produced an "activated catalyst".

A vanadium phosphorus oxide catalyst was prepared in the same manner with untreated boron nitride. The treated and untreated boron nitride catalysts contained 30 wt % vanadium phosphorus oxide.

Catalytic testing was carried out as described above in Comparative Example 1 for all catalysts. The yield of maleic anhydride versus temperature is shown in FIG. 1 for Example 1 (vanadium phosphorous oxide on phosphate boron nitride), Example 2 (vanadium phosphorus oxide supported on boron nitride) and for Comparative Example 2 (vanadium phosphorus oxide). As can be seen from FIG. 1, yields for maleic anhydride obtained from vanadium phosphorus oxide supported on phosphated boron nitride catalysts increase at higher temperatures, in sharp contrast to the behavior of vanadium phosphorus oxide (Comparative Example 2) The phosphorus-modified boron nitride catalyst provides increasing yields with temperature. The percentage yield of maleic anhydride using the untreated boron nitride catalyst plateaus (or slightly decreases) at temperatures greater than 400° C.

As shown in FIG. 1, at temperatures above 400° C., the % yield to maleic anhydride begins to decrease for the conventional VPO catalyst (Comparative Example 2), while it is still increasing for the vanadium phosphorus oxide catalyst supported on phosphated boron nitride (Example 1). In the case of the boron nitride system, pre-phosphating BN offering a significant improvement in the percentage yilelds to maleic anhydride at temperatures above 425° C. As indicated below, vanadium phosphorus oxide supported on untreated boron nitride Example 2) also shows improvement in higher temperature performance (above 425° C.) compared to vanadium phosphorus oxide (Comparative Example 2), but this improvement is not as pronounced as it is for the vanadium phosphorus oxide supported on phosphated boron nitride (Example 1).

EXAMPLE 2

Exactly the same procedure was followed to prepare VPO on non-phosphated boron nitride. As shown in FIG. 1, this material showed an increase in maleic anhydride yield, but tended to level off at about 20%. It still showed improvement over VPO catalyst (Comparative Example 2), which did not contain boron nitride at temperatures above about 420° C., as indicated in FIG. 1 and as described above.

EXAMPLE 3

The process of Comparative Example 1 was repeated to provide a catalyst containing 30 wt % vanadium phosphorus oxide combined with silicon nitride (Si3N4=0.074 mm; Strem, 93–1442).

Figure 2:
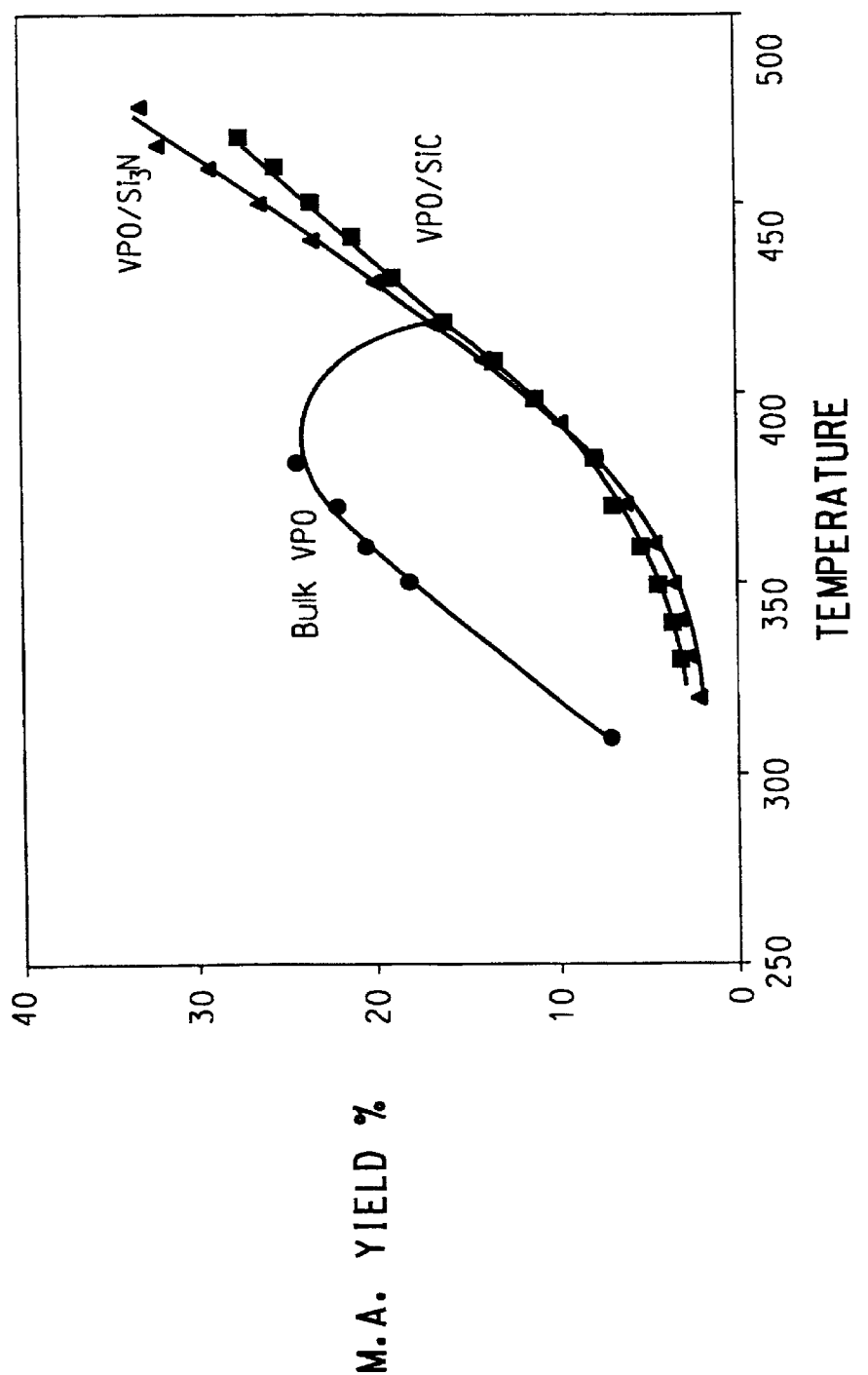
FIG. 2 is a plot of the yield of maleic anhydride versus reaction temperature for the oxidation of n-butane using vanadium phosphorus oxide catalyst combined with silicon nitride (Si3N4=0.074 mm; Strem, 93–1442). A comparison is also made to the comparative catalyst (Comparative Example 1), vanadium phosphorus oxide supported on silicon carbide and Comparative Example 2 (vanadium phosphorus oxide).

Catalytic testing was carried out as described above in Comparative Example 1 for vanadium phosphorus oxide supported on SiC. These testing protocols were applied to conventional VPO catalyst (Comparative Example 2), vanadium phosphorus oxide supported silicon nitride (Example 3) and the catalyst of Comparative Example 1 (vanadium phosphorus oxide supported on silicon carbide). The percentage yield of maleic anhydride versus temperature is shown in FIG. 2 for these catalysts. As can be seen from FIG. 2, the catalyst of Example 3 exhibits superior higher temperature performance (above 425° C.) compared with vanadium phosphorus oxide (Comparative Example 2). This behavior is similar to that observed from catalysts prepared in Example 1 (vanadium phosphorus oxide supported on phosphated boron nitride), in which the percentage yield to maleic anhydride increases with temperature, up to 470° C.

What is claimed is:

1. A process for preparing a catalyst comprising vanadium phosphorus oxide combined with a thermally conductive material, comprising the steps of:

a) forming a suspension comprising a vanadium (IV) phosphate compound in a liquid medium;

b) adding a thermally conductive material to the suspension under agitation at a temperature between 40° C. and 120° C. to provide vanadium (IV) phosphate combined with the thermally conductive material;

c) drying the vanadium (IV) phosphate/thermally conductive material;

d) optionally washing the dried vanadium (IV) phosphate/thermally conductive material with water; and e) calcining the vanadium (IV) phosphate/thermally conductive material either in situ or ex situ at elevated temperature to obtain a catalyst comprising vanadium phosphorus oxide combined with a thermally conductive material, wherein forming the suspension comprising a vanadium (IV) phosphate compound in a liquid medium comprises heating vanadium pentoxide with at least one substantially anhydrous unsubstituted alcohol having 1–10 carbon atoms, 1–3 hydroxyl groups and free from olefinic double bonds to form a feed of vanadium pentoxide reduced to a valence between 4 and 4.6, and then contacting the feed with a solution of orthophosphoric acid and at least one substantially anhydrous unsubstituted alcohol having 1–10 carbon atoms, 1–3 hydroxyl groups and free from olefinic double bonds.

2. A process for preparing a catalyst comprising vanadium phosphorus oxide combined with a thermally conductive material, comprising the steps of:

a) forming a suspension comprising a vanadium (IV) phosphate compound in a liquid medium;

b) adding a thermally conductive material to the suspension under agitation at a temperature between 40° C. and 120° C. to provide vanadium (IV) phosphate combined with the thermally conductive material;

c) drying the vanadium (IV) phosphate/thermally conductive material;

d) optionally washing the dried vanadium (IV) phosphate/thermally conductive material with water; and e) calcining the vanadium (IV) phosphate/thermally conductive material either in situ or ex situ at elevated temperature to obtain a catalyst comprising vanadium phosphorus oxide combined with a thermally conductive material, wherein forming the suspension comprising a vanadium (IV) phosphate compound in a liquid medium comprises the hydrochloric acid digestion of $V_2O_5$ and $H_3PO_4$ in an aqueous solvent.

3. The process of claim 1, or claim 2, wherein step b) is conducted at a temperature of 80° C.

4. The process of claim 1 or claim 2 wherein the dried vanadium (IV) phosphate/thermally conductive material is washed with water.

5. A process for the oxidation of a hydrocarbon comprising contacting a hydrocarbon with a catalyst comprising vanadium phosphorus oxide combined with a thermally conductive material wherein the contacting is performed at a temperature of from 400° C. to 650° C.

6. The process of claim 5 wherein the hydrocarbon is selected from the group consisting of alkanes, olefina and aromatic compounds.

7. The process of claim 6, wherein the hydrocarbon is n-butane.

* * * * *